(12) United States Patent
Pusch et al.

(10) Patent No.: US 8,317,874 B2
(45) Date of Patent: Nov. 27, 2012

(54) ORTHOPEDIC FLUID DAMPER AND METHOD

(75) Inventors: Martin Pusch, Duderstadt (DE); Jens Noerthemann, Duderstadt (DE); Thomas Kettwig, Goettingen (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 143 days.

(21) Appl. No.: 12/668,507

(22) PCT Filed: Jul. 9, 2008

(86) PCT No.: PCT/DE2008/001128
§ 371 (c)(1),
(2), (4) Date: Jan. 11, 2010

(87) PCT Pub. No.: WO2009/006886
PCT Pub. Date: Jan. 15, 2009

(65) Prior Publication Data
US 2010/0191347 A1 Jul. 29, 2010

(30) Foreign Application Priority Data

Jul. 9, 2007 (DE) .......................... 10 2007 032 090

(51) Int. Cl.
*A61F 2/64* (2006.01)
*A61F 2/74* (2006.01)
*A61F 5/01* (2006.01)
(52) U.S. Cl. ................. 623/46; 623/44; 602/26; 602/16
(58) Field of Classification Search .................. 623/27, 623/44, 39, 43, 45, 46; 602/5, 16, 26
See application file for complete search history.

(56) References Cited

U.S. PATENT DOCUMENTS

| | | | | | |
|---|---|---|---|---|---|
| 2,619,652 | A | * | 12/1952 | Vesper | 623/26 |
| 3,417,409 | A | * | 12/1968 | Prahl | 623/26 |
| 4,206,519 | A | * | 6/1980 | Blatchford et al. | 623/44 |
| 5,092,902 | A | | 3/1992 | Adams et al. | |
| 8,048,172 | B2 | * | 11/2011 | Jonsson et al. | 623/24 |

(Continued)

FOREIGN PATENT DOCUMENTS

DE 30 28 608 7/1980

(Continued)

*Primary Examiner* — William H Matthews
*Assistant Examiner* — Marcia Hoffman
(74) *Attorney, Agent, or Firm* — Whitham Curtis Christofferson & Cook, PC

(57) ABSTRACT

The invention relates to an orthopaedic aid, in particular to a prosthesis (58) or orthosis comprising an orthopaedic fluid damper (10) with a displacement chamber (14) formed in a housing (12), with a piston (16) mounted in the displacement chamber (14), with a fluid reservoir for a fluid (20), with a return flow conduit (22) connecting the displacement chamber (14) to the fluid reservoir, with a valve (24) that can adopt an open position and a closed position, in which it at least partially closes the return flow conduit (22), and with a joint (72) that has a first branch (60) and a second branch (66), wherein the first branch (60) is connected to the housing (12) and the second branch (66) is connected to the piston (16). A device (84) is also provided for detecting a joint force (FB) acting on the joint, which device (84) is designed to bring the valve (24) to the closed position when the joint force (FB) exceeds a predefined threshold value. The invention also relates to a method for control of the aid and a fluid damper (10) fitted therein.

21 Claims, 13 Drawing Sheets

U.S. PATENT DOCUMENTS

2002/0152750 A1 * 10/2002 Asai et al. .................. 60/520

FOREIGN PATENT DOCUMENTS

| | | |
|---|---|---|
| DE | 3028608 | 2/1982 |
| DE | 19859931 | 7/2000 |
| DE | 10214357 | 10/2003 |
| DE | 102005020188 | 11/2006 |
| EP | 0309441 | 9/1988 |
| EP | 0654254 | 9/1994 |
| EP | 1348409 | 1/2003 |
| WO | WO2007/016408 | 7/2006 |

* cited by examiner

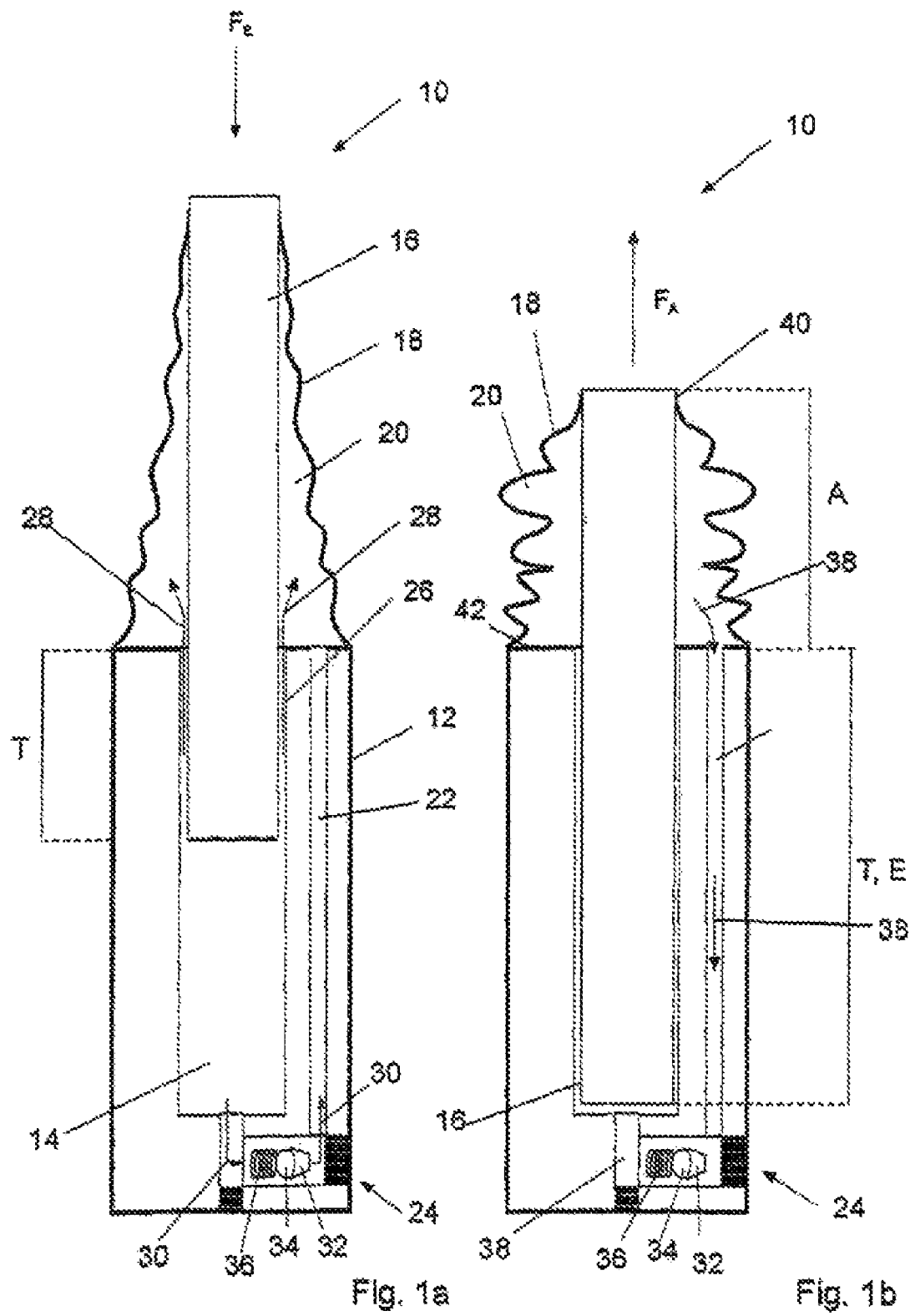

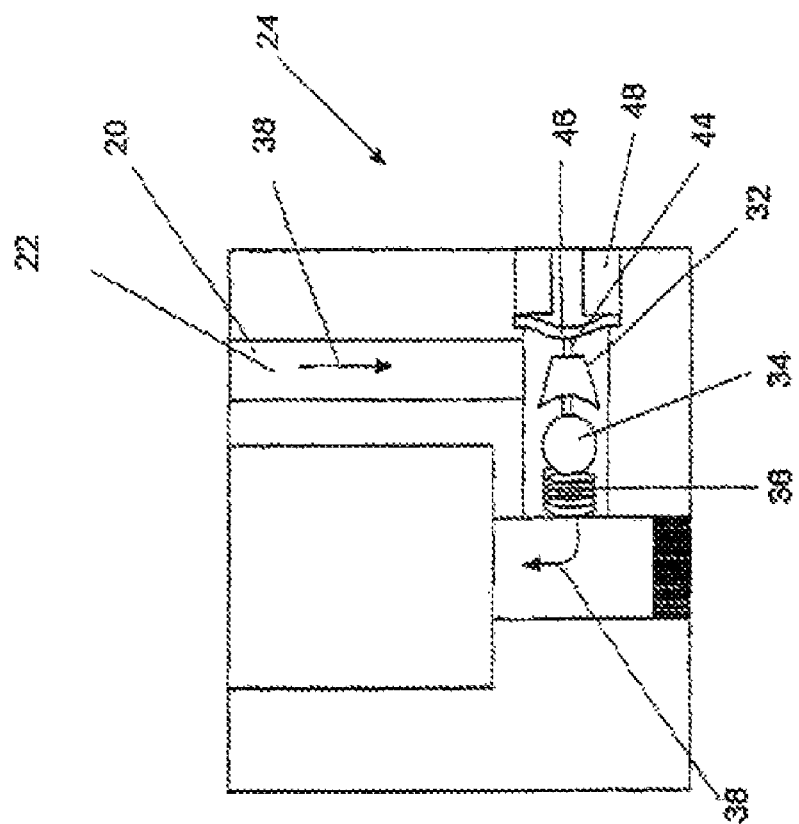
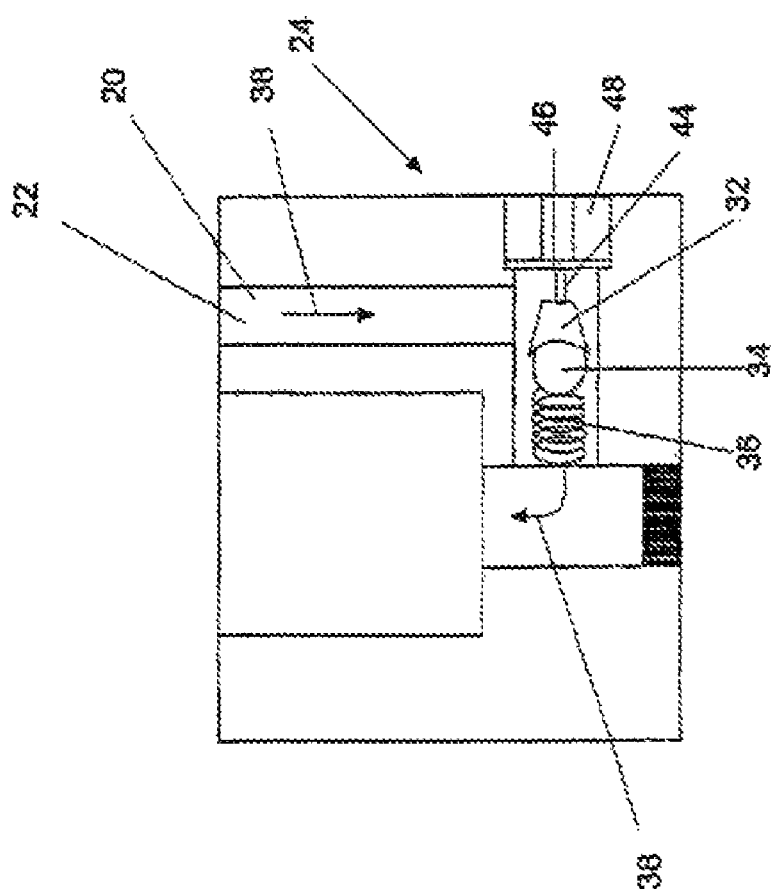

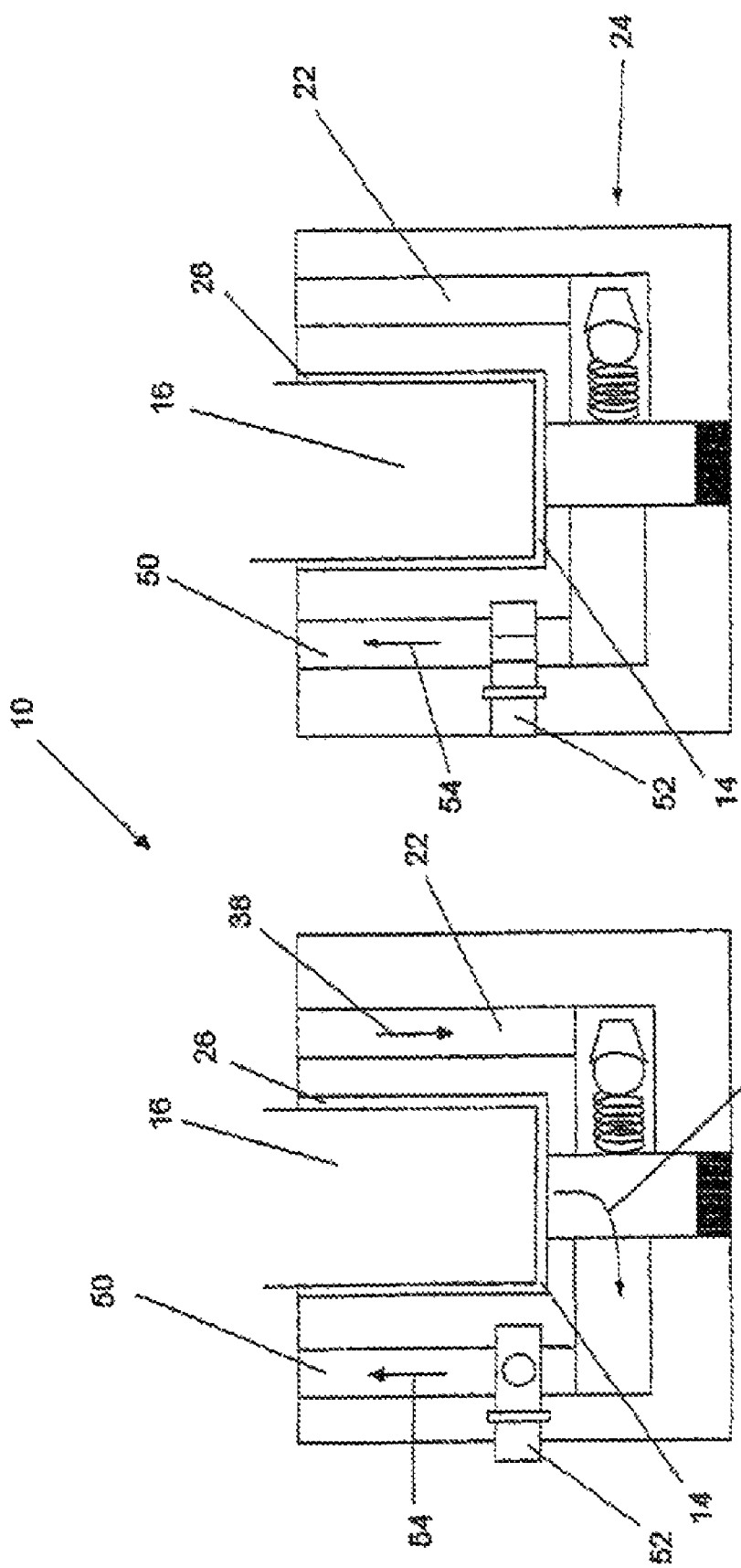

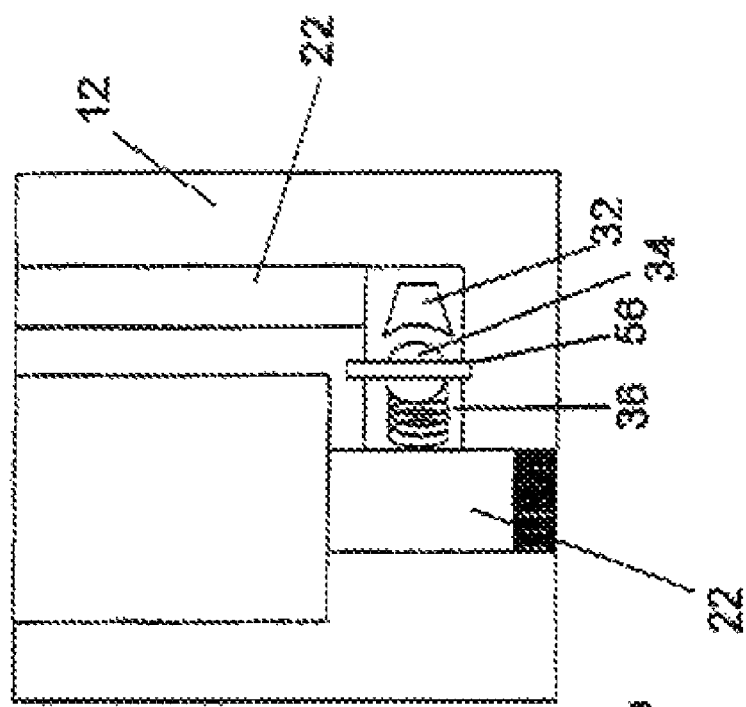
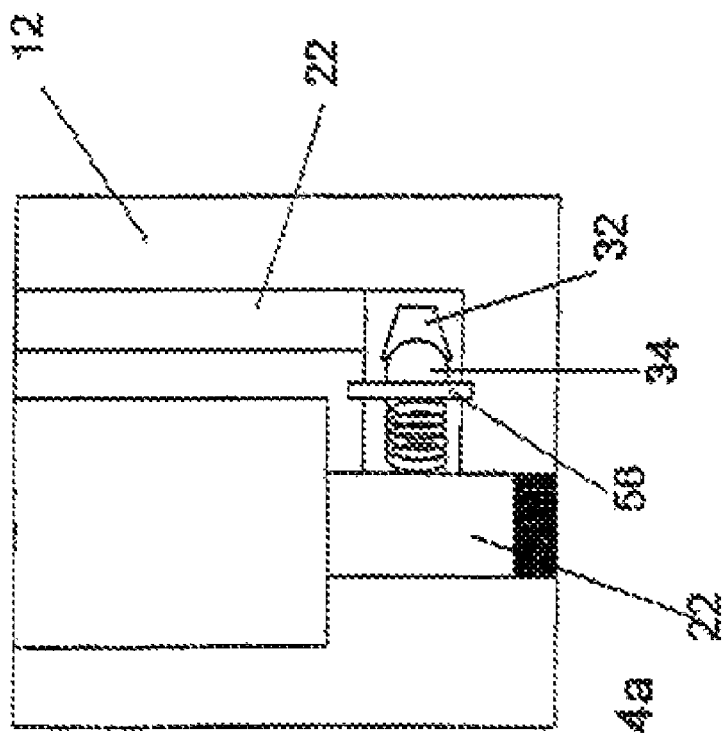

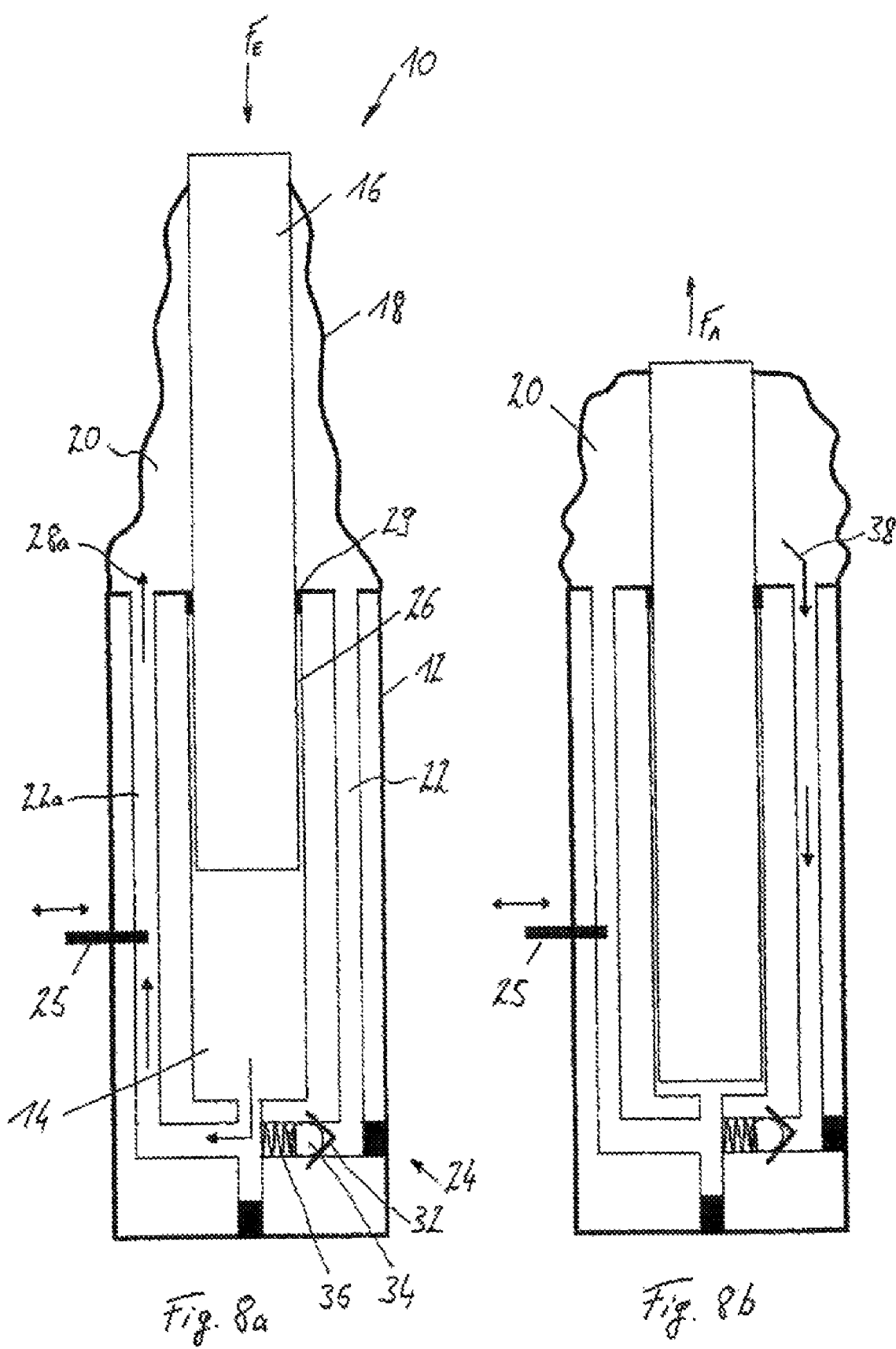

ORTHOPEDIC FLUID DAMPER AND METHOD

BACKGROUND OF THE INVENTION

1. Field of the Invention

The invention relates to an orthopaedic fluid damper and to an orthopaedic aid with such a damper which is designed for use in a prosthesis or orthesis, with a displacement chamber formed in a cylinder housing, with a piston mounted in the displacement chamber, with a fluid reservoir for a fluid, with a backflow line which connects the displacement chamber to the fluid reservoir, and with a valve which can assume an opening position and a closing position, in which it at least partially closes the backflow line. According to a further aspect, the invention relates to a method for controlling the orthopaedic aid.

2. Description of Related Art

Orthopaedic fluid dampers are employed in orthopaedic aids, such as, for example, prostheses or ortheses. They serve as a resistance element between two limbs. For example, the orthopaedic fluid damper is arranged between a thigh and a lower leg of a leg prosthesis and increases a bending resistance of a knee joint of the leg prosthesis.

Leg prostheses with orthopaedic fluid dampers of this type are rarely found in geriatric patients. For patients of great age who are severely restricted in their muscular and motor capability, blocking knee joints are often employed.

Known orthopaedic blocking knee joints for geriatric leg prostheses provide geriatric patients with only two states, blocked or unblocked, for cost reasons. The geriatric patient prefers the blocking knee joint which is blocked by means of the lock. Known orthopaedic blocking joints have the disadvantage that they cause the patient's gait to have a hobbling appearance, since the patient brings the leg forward by rotating it outwardly (circumduction) or lengthens the healthy leg via a pointed-foot position or slanted-hip position, so that the leg prosthesis can swing through freely. So that he can sit down, the geriatric patient releases the lock manually. In this state, the leg prosthesis offers no bending resistance and therefore, disadvantageously, also no longer any safety. The patient has to support himself with both hands in this situation. Moreover, should the geriatric patient stumble when the leg prosthesis is released, he involuntarily falls down. For this reason, known orthopaedic aids which are equipped with conventional orthopaedic locks are unpopular among geriatric patients.

EP 0 309 441 discloses a double-acting hydraulic piston/cylinder unit, by means of which the outer dimensions of a concertina preserve an approximately predetermined form, the concertina spanning large parts of the piston/cylinder unit. The disadvantage of this piston/cylinder unit is that it is complicated to produce.

DE 102 14 357 A1 discloses a prosthetic knee joint with a hydraulic damping cylinder. In the prosthetic knee joint, a hydraulic fluid is present, the viscosity of which can be varied via an external force field. The disadvantage of this embodiment is that, although it makes increased walking comfort possible, it nevertheless requires an electric control, which, however, is not justifiable for low-priced prostheses.

DE 198 59 931 A1 discloses a leg prosthesis which is likewise damped to a greater or lesser extent via a hydraulic fluid, the viscosity of which can be varied by means of external electrical fields. The disadvantage here, too, is that a control is necessary.

BRIEF SUMMARY OF THE INVENTION

The object on which the invention is based is to provide an orthopaedic fluid damper, by means of which orthopaedic aids can be produced which are more readily acceptable to geriatric patients.

The invention solves the problem by means of an orthopaedic aid having the features of the main claim, which comprises an orthopaedic fluid damper according to the invention and a joint which has a first limb and a second limb, the first limb being connected to the cylinder housing and the second limb being connected to the piston of the fluid damper and having a device which detects the force acting on the joint, in order to bring the valve into a closing position when a threshold value is overshot. According to a second aspect, the invention solves the problem by means of a method according to the invention for controlling an orthopaedic aid according to the invention, having the steps (a) detection of a force (joint force) acting on the joint or the prosthesis and (b) activation of the valve in such a way that it at least partially closes the backflow line. According to a third aspect, the invention solves the problem by means of a generic orthopaedic fluid damper, in which the piston is mounted in the displacement chamber at at least one push-in depth, so as to form an annular gap, in particular a throughflow-determining annular gap.

An orthopaedic aid preferably comprises a device for detecting the load acting on the prosthesis, which is designed in order to bring, the valve into the closing position when the joint force overshoots a preset threshold value. This device may, for example, be a sensor which detects a force or a torque. However, the device may also be formed by a purely mechanical connection.

The orthopaedic aid is preferably a leg prosthesis with a knee joint and with a device for detecting the load acting on the prosthesis. This device comprises a leg-axis force sensor which detects the leg-axis force acting in the longitudinal direction of the extended leg prosthesis.

So that the leg-axis force can be determined especially accurately and sensitively, a front-foot force sensor arranged in a front foot of a foot of the leg prosthesis and/or a back-foot force sensor arranged in a back foot are preferably provided. These are connected electrically to an electric control which activates the valve as a function of electrical signals which said control receives from the sensors.

The leg-axis force sensor may be designed as a carrying element of the prosthesis which, for example, changes its longitudinal extent as a function of the load upon the leg prosthesis. Alternatively, the leg force sensor may comprise strain gages.

Alternatively to an electronic measurement, evaluation and actuation, there is provision for the device for detecting the joint force to be set up mechanically and, in the event of load, to displace the valve into the closing position. The mechanical control may take place, for example, via relative displacement of the limbs with respect to one another, in that a pivoting or axial displacement of the limbs with respect to one another is utilized and, for the displacement of the valve, the forces occurring are at least partially transmitted to this. For this purpose, the device for detecting the joint force may be designed as a buckling spring, spring shackle, cam guide or slotted guide or as a lever system, via which the displacement forces are transmitted to the valve. Preferably, the device is coupled to a solenoid valve which is prestressed in the direction of the closing position, so that, when a switching magnet is removed, the valve is closed automatically. This ensures that, in the event of a failure of the mechanism, damping is increased abruptly, thus ensuring the stability of the joint.

The switching movement may take place in that the limbs are displaced toward one another in the case of a sufficiently high axial force component. For this purpose, the two limbs are mounted one on the other so as to be displaceable to a limited extent in relation to one another, as a result of which, in the event of mechanical switching, the valve is actuated directly, while, in the event of sensor switching, the displacement travel is detected as a variable to be sensed, via which an actuator signal is triggered. The displacement indicates an axial forte load, for example when a prosthesis user is standing, so that safety during a standing phase can be provided via an increase in damping. To counteract the displacement movement, a spring acting in the axial direction may be provided, which compensates tolerances and causes a return movement into the initial state.

In a development of the invention, the damper and the joint are mounted together on a frame or form said frame which is displaceable, in particular shiftable, in relation to one of the limbs. Between the frame and one of the limbs, a spring may be arranged which acts counter to a displacement of the limb towards the frame. The hydraulic damper may be designed as a single-acting or double-acting damper, as a cylinder damper or as rotary hydraulics.

In addition to a control dependent on axial force, it is additionally possible that, and there is provision whereby, the device is designed such that a displacement, dependent on the pivot angle $\phi$, of a switching element in relation to the valve takes place, but preferably not solely by mechanical coupling.

Within the scope of a method according to the invention, the valve is preferably activated such that it at least partially closes the backflow line when the leg-axis force overshoots a preset closing threshold value. For this purpose, it is possible, but not necessary, that the closing threshold value is explicitly stored, for example, in the electric control. It is also possible that a degree of closing of the valve is dependent monotonically or continuously on the leg-axis force, that is to say the valve is closed the further, the higher the leg-axis force is.

Furthermore, there is provision whereby, in a variant of the invention, the valve is switched independently of the position of the limbs, that is to say it is unimportant how the limbs stand in relation to one another or in space, but, instead, the aim is merely to ensure that a sufficiently high axial force component is present. Whether bending moments, torsional moments or horizontal forces also occur in the orthopaedic aid is then insignificant.

In a further variant, the valve is switched as a function of the angle $\phi$ of the limbs with respect to one another, for example in the case of a bending angle of between 20° and 50° with respect to one another. If a certain fixed bending angle is reached in the case of use in a leg prosthesis, damping is automatically increased, in order to ensure that the joint is secured. Damping may in this case be set such that a slow lowering is still possible. The switching of the valve on account of a displacement or pivoting of the limbs with respect to one another takes place, for example, mechanically, in that a relative movement of the limbs with respect to one another is transmitted to the valve.

A fluid damper according to the invention has the advantage that it makes it possible to produce an orthopaedic aid which satisfies the needs of geriatric patients. When the prosthesis is loaded, high damping is available to the patient, which avoids sudden buckling and allows safe walking. Under load, the piston displaces the fluid slowly through the annular gap out of the displacement chamber into the pressureless fluid reservoir. The patient subsides slowly in the knee joint and always has the feeling of being supported by the leg prosthesis. Moreover, an unlocking of the fluid damper is dispensed with.

If, by contrast, no load or bending force is applied to the knee joint of the leg prosthesis, the valve can be brought into the opening position and the leg swings through without resistance. There is therefore no need to bring the leg prosthesis forward by rotating it outward or to lengthen the healthy leg via the pointed-foot position. The gait therefore appears more natural.

A further advantage is that the orthopaedic fluid damper according to the invention can be produced by simple technical means. In conventional fluid dampers, a good sealing action between the piston and displacement chamber must be ensured. Such a seal is complicated and cost-intensive. Since, according to the invention, an annular gap is provided, markedly lower manufacturing tolerances can be provided in the manufacture of the piston and cylinder housing, thus making manufacture easier and less costly.

Moreover, on account of the acceptable lower manufacturing tolerances, it is possible to use cost-effective materials, such as, for example, plastic, which have a low modulus of elasticity, in order to produce the cylinder housing and/or the piston. In conventional fluid dampers, leaktightness between the piston and displacement chamber also has to be ensured under mechanical load. In order under mechanical load to prevent a play which puts leaktightness at risk, materials with a high modulus of elasticity, such as, for example, metals, have to be used. This necessity is avoided in the fluid damper according to the invention.

An annular gap is understood, within the scope of the present description, to mean, in particular, an interspace between an inside of the displacement chamber and an outside of the piston. This annular gap may, but must not necessarily, have an annular cross section. It is possible that the piston bears in regions against the inner wall and the cross section of the annular gap is therefore crescent-shaped. A further possibility is that the piston bears in wide regions against the inner wall and possesses longitudinal grooves, through which the fluid can pass from the displacement chamber into the fluid reservoir. Contrary to known fluid dampers, in which annular gaps can occur only due to manufacturing tolerances, in the fluid damper according to the invention, the piston is manufactured such that it forms an annular gap of preset cross-sectional area with the cylinder housing or such that the fluid experiences a preset fluid resistance when it flows through the annular gap. In other words, in known fluid dampers, the piston and cylinder housing form a sealing fit, whereas, in the fluid damper according to the invention, a loose clearance fit may be formed. In known fluid dampers, therefore, this results at most in leakage streams, but not, as in the fluid damper according to the invention, defined damping fluid streams.

It is possible, but not necessary, that the piston and cylinder housing form an annular gap of identical cross-sectional area in all cross sections perpendicular to the piston longitudinal axis.

In a preferred embodiment, the valve leads to a damping of the movement of the piston in the displacement chamber, the damping acting in only one direction of movement of the piston, for example in the push-in direction of the piston into the cylinder housing. In the case of use in an orthopaedic aid, it is usually necessary, but also sufficient, to damp a movement of two limbs of a joint of the aid in the push-in direction. If the orthopaedic fluid damper is installed in a leg prosthesis, this is the bending direction (flexion direction). In order to implement the feature, the valve may, for example, be a nonreturn valve, this being simple and cost-effective.

The fluid, when it flows along a fluid path out of the displacement chamber through the annular gap into the fluid reservoir, experiences an annular-gap fluid resistance and, when it flows along a fluid path out of the displacement chamber through the backflow line into the fluid reservoir, experiences a backflow fluid resistance. There is preferably provision for the annular gap to possess a form and/or cross-sectional area which is dimensioned such that, when the valve is in the closing position, the annular-gap fluid resistance is lower than the backflow fluid resistance. That is to say, with the valve closed, when the piston is pushed into the displacement chamber, more fluid passes through the annular gap into the fluid reservoir than through the backflow line.

Particularly preferably, the valve and the annular gap are designed such that, when the valve is in the closing position and the piston is pushed into the displacement chamber, essentially the entire fluid flows out of the displacement chamber through the annular gap into the fluid reservoir. The feature that essentially the entire fluid flows in the way described is to be understood as meaning that it is not necessary for the entire fluid to flow through the annular gap in the strict sense. On the contrary, it is possible that a small part stream continues to flow through the valve. This part stream is, for example, lower than 15% of the overall stream.

Particularly preferably, the fluid is a hydraulic fluid. This hydraulic fluid may be an oil, for example, mineral oil, but, for example, also water. The use of air is also possible in principle.

It is beneficial if the viscosity of the hydraulic fluid is independent of magnetic fields and/or electrical fields. This system may be understood as meaning that the viscosity changes, in particular, by less than 50% when a magnetic field of 0.1 Tesla is applied. In particular, the hydraulic fluid is free of magnetic particles. Such hydraulic fluids are especially cost-effective.

A fluid damper which is especially simple and cost-effective to manufacture is obtained when the cylinder housing and/or the piston are/is manufactured, in particular injection-molded, from plastic. A further advantageous configuration comprises a cylinder housing with a metal sleeve injected or embedded into the plastic. The metal sleeve in this case forms the cylinder. This combination reduces the deformation of the cylinder under load. In order to avoid the alternative deformation of the cylinder, the cylinder housing may be surrounded from outside by composite fiber materials. This advantageously allows a cost-effective mass production of simple orthopaedic aids, which also makes them available to patients in countries where the income is low.

During use, the piston of the fluid damper is regularly pushed into the displacement chamber and pulled out of this. In other words, a push-in depth of the piston, that is to say the length of the distance over which the piston is pushed into the displacement chamber, changes constantly. Advantageously, the damping by which the fluid damper opposes a further pushing of the piston into the displacement chamber can be varied in that the piston has a contoured configuration. For example, the piston may taper conically, a cross-sectional area of the piston becoming larger, for example, with an increasing push-in depth. In this case, the resistance with which the fluid damper opposes a further pushing of the piston into the displacement chamber rises with the push-in depth. Installed in a leg prosthesis, this has the effect that a bending of the knee joint is damped especially highly toward the end of the sitting down of the patient.

Moreover, it is possible that the diameter of the piston decreases with an increasing push-in depth. It is also possible that the piston has a convex or concave design. All the forms mentioned may also be present in portions, and therefore the piston may, for example, possess a conical portion and a cylindrical portion.

Alternatively, or additionally, moreover, the displacement chamber has a contoured configuration. This is to be understood as meaning that an inner wall of the displacement chamber may, as outlined above, be designed conically, convexly, concavely and/or, in portions, cylindrically.

A fluid damper which is especially simple to manufacture is obtained when the fluid reservoir is designed in order to store the fluid so that it is always essentially pressure-free. Moreover, a loss of fluid is thereby largely avoided. Particularly preferably, the fluid reservoir is a concertina. Such a concertina can be manufactured very easily. The piston has a penetration portion, which can penetrate into the cylinder housing, and a fine portion, which cannot penetrate into the cylinder housing. There is preferably provision for the concertina to be fastened to the cylinder housing and to the free portion. Thus, the concertina is fastened securely and can easily be exchanged for maintenance purposes. However, it is basically also possible to store the fluid under pressure.

A fluid reservoir formed by a concertina is put at risk by mechanical actions, and therefore the fluid reservoir is preferably surrounded by a sleeve, in particular a plastic sleeve, which advantageously has at least one pressure compensation orifice, so that the concertina can expand or a diaphragm can variably form a reception volume.

To actuate the valve, the orthopaedic fluid damper preferably possesses a magnet arranged outside the cylinder housing, the valve being capable of being brought from the opening position to the closing position by means of the magnet. Switching via a magnet may also be used in other types of fluid damper, in which there is no annular gap present or which have a double-acting set-up or are set up as rotary hydraulics. This may be implemented, for example, in that the magnet is an electromagnet which cooperates with a ferromagnetic valve ball of the valve. This takes place, for example, in that an application of current to the electromagnet moves the valve ball such that the valve is brought into the opening position or alternatively into the closing position. Alternatively, there is provision for the magnet to be a permanent magnet which is mounted displaceably and in an automatically actuable way via an actuator arranged outside the cylinder housing or via mechanical coupling and which cooperates with the valve ball.

According to the invention, moreover, a generic orthopaedic fluid damper, in which the cylinder housing and/or the piston are/is manufactured, in particular injection-molded, from plastic, is provided. Such a fluid damper preferably has the feature of the characterizing part of claim 23 and/or one or more of the abovementioned features. There may then be provision for the piston to be mounted in the displacement chamber via a seal, for example an O-ring seal. In this case, in addition to the backflow line, a further line may be provided which connects the fluid reservoir to the displacement chamber.

Embodiments of the invention are explained in more detail below with reference to the accompanying drawings. The same reference symbols designate identical or identically acting components or elements in the figures. In these:

BRIEF DESCRIPTION OF THE DRAWINGS

FIG. 1*a* shows an orthopaedic fluid damper according to the invention in a cross-sectional view, in which a piston is pushed into the displacement chamber to a low push-in depth, FIG. 1b shows the fluid damper according to FIG. 1a, in which the piston is pushed essentially completely into the displacement chamber, FIG. 2a shows, in the form of a detail, a diagrammatic sectional view of the valve of the fluid damper from FIGS. 1a and 1b in a closing position, FIG. 2b shows the valve according to FIG. 2a in an opening position, FIG. 3a shows the sectional view of a valve of a further embodiment of an orthopaedic fluid damper according to the invention with a bypass line in which is arranged a bypass valve which is closed, FIG. 3b shows the valve according to FIG. 3a in an opening position, FIG. 4a shows a sectional view of a valve of a further embodiment of an orthopaedic fluid damper according to the invention with an electromagnet in the dead state, FIG. 4b shows the valve according to FIG. 4a in the live state, FIGS. 8a, 8b show a variant of the fluid damper in two positions.

DETAILED DESCRIPTION OF THE INVENTION

Figure 5:
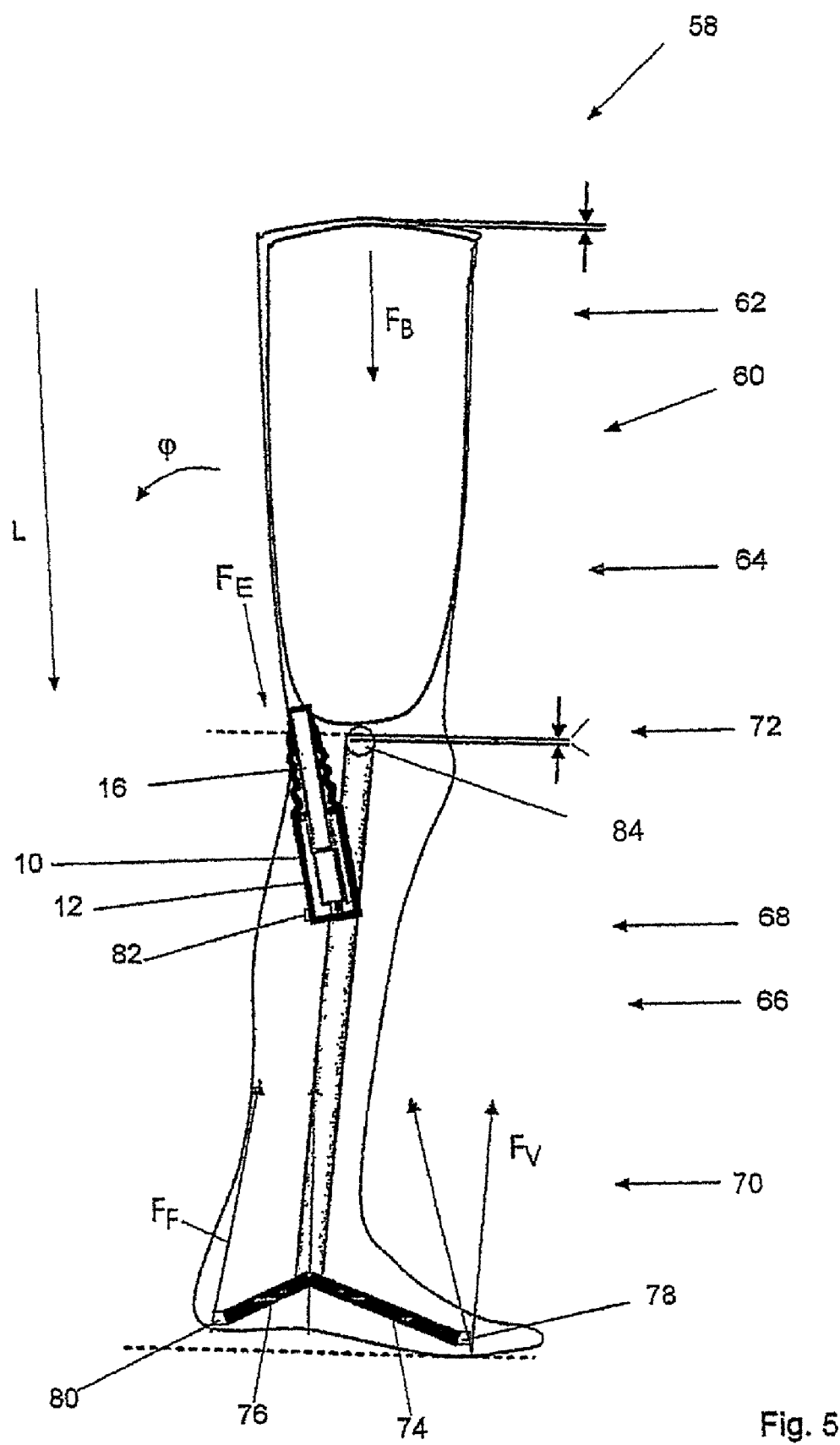
FIG. 5 shows an orthopaedic aid according to the invention in the form of a leg prosthesis in an extended position.

FIG. 1a shows an orthopaedic fluid damper 10 which comprises a cylinder housing 12 made from a plastic with a displacement chamber 14 formed therein, a piston 16 mounted in the displacement chamber 14 and consisting of plastic, a fluid reservoir in the form of a concertina 18, manufactured from elastomer, for a fluid in the form of a hydraulic fluid 20, a backflow line 22 formed in the cylinder housing 12, and a valve 24. The piston 16 is designed cylindrically and is mounted in the cylinder housing 12 so as to form an annular gap 26. The valve 24, which is shown diagrammatically in FIG. 1a in a closing position, comprises a valve seat 32, a valve ball 34 and a helical spring 36 which prestresses the valve ball 34 onto the valve seat 32.

The cylinder housing 12 and the piston 16 may alternatively also consist of aluminum or high-grade steel or comprise, as a liner, a metal sleeve which is embedded in plastic or around which plastic is injection-molded.

The distance which the piston 16 has covered in the cylinder housing 12 constitutes a push-in depth T. When the piston 16 is pushed further into the cylinder housing 12 so that the push-in depth T increases, hydraulic fluid 20 present in the displacement chamber 14 is displaced through the annular gap 26 along an annular-gap fluid path 28 into the concertina 18, since a backflow-line fluid path 30 through the backflow line is shut off by the valve 24.

The hydraulic fluid 20 experiences along the annular-gap fluid path 28 an annular-gap fluid resistance which is dependent on a speed at which the piston 16 is pushed into the cylinder housing 12. This speed depends, in turn, on a push-in force $F_E$ with which the piston 16 is pushed in. The movement of the piston 16 into the cylinder housing 12 is thus damped by the annular-gap fluid resistance.

FIG. 1b shows a piston 16 which is pushed essentially completely into the displacement chamber 14 and which is pulled out of the displacement chamber 14 by means of a pull-out force $F_A$. Hydraulic fluid 20 flows out of the concertina 18 along a backflow path 38 through the valve 24 into the displacement chamber 14. The valve 24 is designed as a nonreturn valve and allows hydraulic fluid 20 free passage in this direction.

Moreover, FIG. 1b shows a penetration portion E of the piston 16 and a free portion A which cannot penetrate into the cylinder housing 12. The concertina 18 is fastened, on the one hand, to an end 40 of the piston 16 which faces away from the cylinder housing 12, and consequently in the free portion A, and, on the other hand, to an end face 42, facing the end 40, of the cylinder housing 12. For example, the concertina is glued on or welded on or engages in each case in grooves, not depicted, in the piston 16 or the cylinder housing 12.

FIG. 2a shows, in the form of a detail, a view of an end, facing away from the piston 16, of the cylinder housing 12. It can be seen that the valve ball 34 can be actuated via an actuator which comprises a pin 44, an actuator diaphragm 46 and an actuator basic body 48. In the non-actuated state which is shown in FIG. 2a, the valve ball 34 lies on the valve seat 32 and prevents a fluid stream out of the displacement chamber 14 into the backflow line 22. By contrast, hydraulic fluid 20 can flow along the backflow path 38 in that it lifts off the valve ball 34 from the valve seat 32 counter to the force of the helical spring 36.

FIG. 2b shows the actuator in an actuation position in which the pin 44 has pressed the valve ball 34 from the valve seat 32. In this position, hydraulic fluid can pass through the valve 24 both along the backflow path 38 and in the opposite direction.

FIG. 3a shows an alternative embodiment of a fluid damper 10 which possesses in addition to the backflow line 22 a bypass line 50 which likewise connects the displacement chamber 14 to the concertina 18, not depicted in FIG. 3a. In this embodiment, no annular gap 26 is necessary. Arranged in the bypass line 50 is a bypass valve 52 which can completely or partially close the bypass line 50 so that a defined fluid resistance can be set. When the piston 16 is pulled out of the cylinder housing 12, hydraulic fluid 20 can flow along the backflow path 38 through the backflow line 22 into the displacement chamber 14. When the piston 16 is pushed into the displacement chamber 14, the hydraulic fluid 20 is displaced through the annular gap 26 into the concertina (cf. FIG. 1a) in the situation shown in FIG. 3a. By contrast, a bypass-line fluid path 54 is shut off by the closed bypass valve 52, and the backflow line 22 is closed by the valve 24.

FIG. 3b shows the situation in which the bypass valve 52 is open so that, when the piston 16 is pushed into the displacement chamber 14, hydraulic fluid can flow along the bypass-line fluid path 54.

FIG. 4a shows an electromagnet 56 which is mounted outside the cylinder housing 12 and which can act on the ferromagnetic valve ball 34. In FIG. 4a, the electromagnet 56 is unenergized, and therefore the valve ball 34 is pressed onto the valve seat 32 by the helical spring 36.

FIG. 4b shows the situation in which the electromagnet 56 is energized and lifts off the valve ball 34 from the valve seat 32. The electromagnet 56 may partially or completely surround the cylinder housing 12 annularly, so that it can cooperate especially effectively with the valve ball 34.

Alternatively, a permanent magnet is provided, which is coupled displaceably to an actuator. A movement of the permanent magnet by means of the actuator leads to a movement of the valve ball 34.

FIG. 5 shows an orthopaedic aid according to the invention in the form of a leg prosthesis 58 which comprises a fluid damper 10 according to the invention, a thigh 60 with a proximal thigh end 62 and a distal thigh end 64, and a lower leg 66 with a proximal lower leg end 68 and a distal lower leg end 70. The thigh 60 and the lower leg 66 are connected to one another in a knee joint 72 and run in a longitudinal direction L in the extended position. The fluid damper 10 is connected by means of its piston 16 to the distal thigh end 64 and by means of its cylinder housing 12 to the proximal lower leg end 68 and causes a damping of a pivoting movement of the thigh 60 in relation to the lower leg 66 over a pivot angle $\phi$. When the thigh 60 pivots in relation to the lower leg 66, the push-in force $F_E$ on the piston 16 is generated, and the damping action described above occurs.

The leg prosthesis 58 possesses a front foot 74 and a back foot 76. A front-foot force sensor 78 for measuring a front-foot force $F_v$ is arranged on the front foot 74, and a back-foot force sensor 80 for measuring a heel force $F_F$ is mounted on the back foot. The two sensors are connected via an electrical line, not depicted, to an electric control 82 which is part of the fluid damper 10. Moreover, the electric control 82 is connected to a leg force sensor 84. The front-foot force sensor 78, the back-foot force sensor 80 and the leg force sensor 84 are designed to determine a leg-axis force $F_B$ which runs from the proximal thigh end 62 to the distal lower leg end 70. The electric control 82 detects the leg-axis force $F_B$, compares this with a closing threshold value or an enabling threshold value, which are stored in an electrical memory of the electric control 82, and, for example, activates the electromagnet 56 (cf. FIG. 4b) on the basis of this comparison. If, for example, the leg-axis force $F_B$ overshoots the preset closing threshold value, this is a sign that the leg prosthesis 58 is loaded by a patient and a high bending resistance is necessary. The electromagnet 56 is then switched off, current-free, by the electric control 82, so that the backflow-line fluid path 30 (cf. FIG. 1a) for the hydraulic fluid 20 is shut off and a high push-in force $F_E$ has to by exerted in order to push the piston 16 into the cylinder housing 12. The leg prosthesis 58 consequently possesses a high bending resistance and affords a high degree of safety to the patient when standing. Moreover, in standing, the leg prosthesis 58 is secured geometrically, since a load line of the applied load runs in front of the knee joint 72 and consequently does not bend the leg prosthesis 58.

Figure 6:
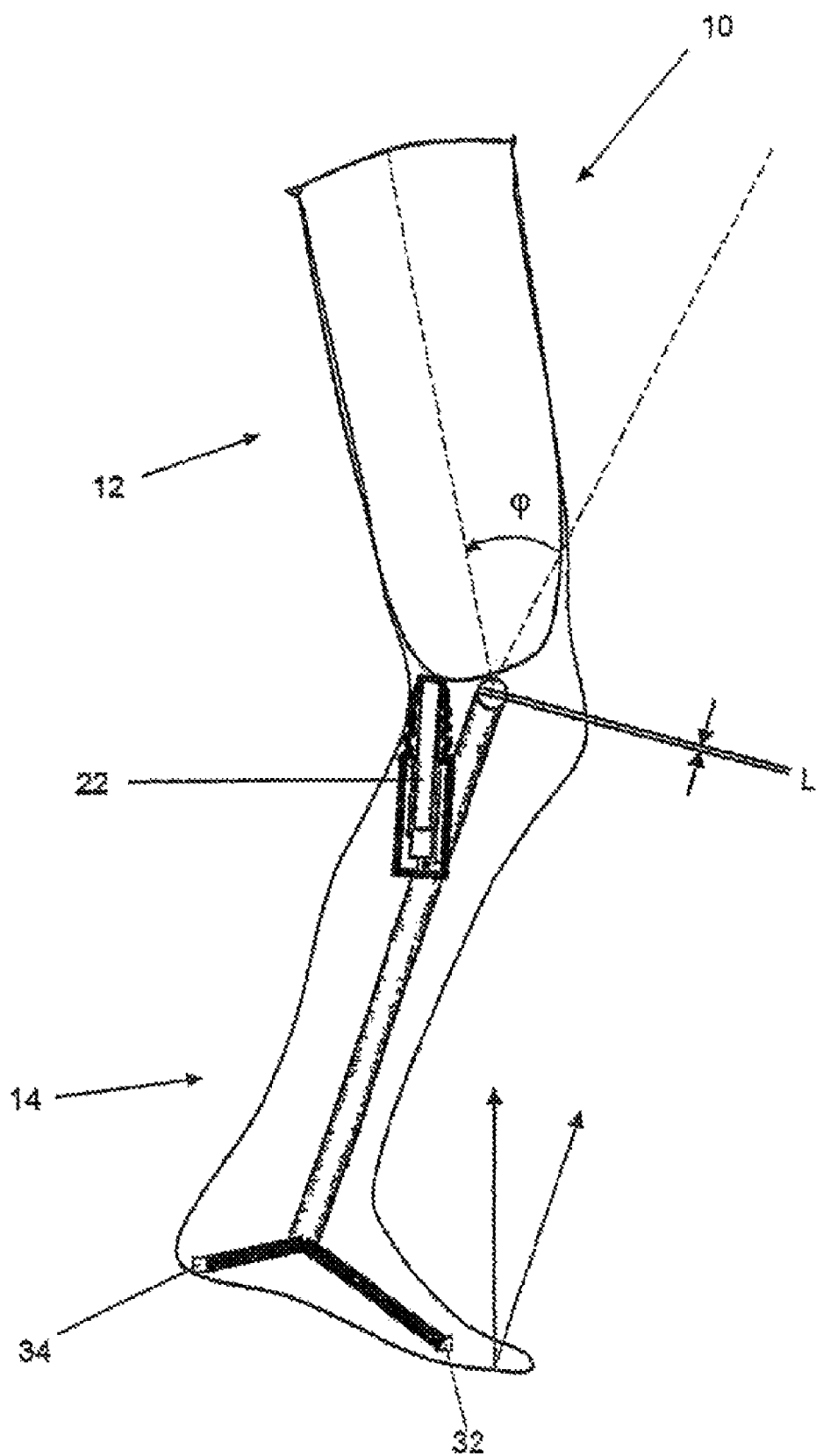
FIG. 6 shows the leg prosthesis according to FIG. 5 in a bent position.

If a markedly higher force prevails on the front-foot force sensor 78 than on the back-foot force sensor 80, this is a sign that the patient would like to sit down, and the electric switch control 82 likewise closes the valve 24. This situation is shown in FIG. 6.

If, however, the leg-axis force $F_B$ is low, the leg prosthesis 56 is non-loaded and the electric control 82 applies current to the electromagnet 56, so that hydraulic fluid can also flow through the backflow-line fluid path 30 (cf. FIG. 1a). The lower leg 66 (FIG. 5) can then swing freely in relation to the thigh 60.

Figure 7A:
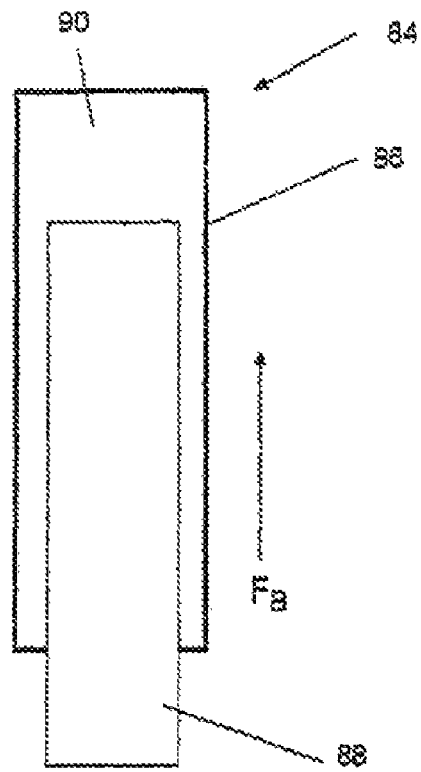
FIG. 7a shows a first embodiment of a leg force sensor.

FIG. 7a shows an embodiment of the leg force sensor 84 with a sleeve 86 into which a measuring piston 88 can be pushed counter to a resistance exerted by a filling material 90 in an adhesive joint. The leg force sensor 84 comprises a means for determining the relative position of the measuring piston 88 in relation to the sleeve 86 which is proportional to the leg-axis force $F_B$.

Figure 7B:
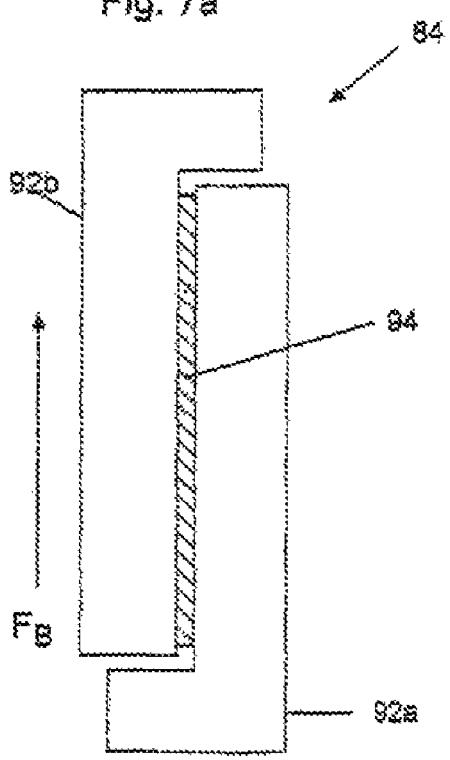
FIG. 7b shows an alternative embodiment of a leg force sensor.

FIG. 7b shows an alternative embodiment of the leg force sensor 84, in which two L-shaped measuring elements 92a, 92b are connected via an elastic element 94. The leg force sensor 94 comprises, once again, a means, not depicted, for determining the relative position of the two measuring elements 92a, 92b in relation to one another, which constitutes a measure of the acting leg-axis force $F_B$.

Figure 7C:
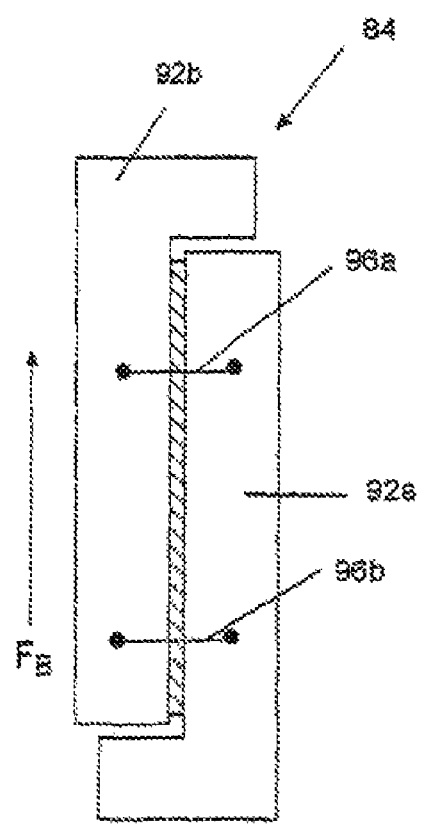
FIG. 7c shows a further alternative embodiment of a leg force sensor.

FIG. 7c shows a further alternative embodiment of the leg force sensor 84 which differs from the leg force sensor shown in FIG. 7b in that the two measuring elements 92a, 92b are connected via two webs 96a, 96b.

FIGS. 8a and 8b illustrate a fluid damper 10 which corresponds essentially to the fluid damper in FIGS. 1a and 1b. Instead of the annular gap 26 which is open and allows a backflow of the hydraulic fluid out of the displacement chamber 14 into the fluid reservoir of the concertina 18, in the variant according to FIGS. 8a and 8b the annular gap 26 is closed via a seal 29. Instead of flowing through the annular-gap fluid path 28 according to the embodiment of FIGS. 1a and 1b, the hydraulic fluid 20 flows out of the displacement chamber 14 through a backflow line 22a, so that a backflow-line fluid path 28a is formed. Within the backflow line 22a is arranged a valve 25 which is preferably designed as a solenoid valve and which can variably change the cross section of the backflow line 22a. The further the valve 25 is opened, the more easily can the hydraulic fluid 20 flow out of the displacement chamber 14 back into the fluid reservoir of the concertina 18, and the further the valve 25 displaces the flow cross section, the higher the resistance against the penetration of the piston 16 becomes. Due to the rise in the push-in force $F_E$, the bending resistance in the knee joint of the leg prosthesis then rises. In addition to a configuration of the valve 25 as a solenoid valve, other valve configurations may also be provided, in particular actuating valves which allow a rapid and simple variation of the flow cross section in the backflow line 22a.

In the exemplary embodiment illustrated, the fluid reservoir is formed by the volume within the concertina 18, while the fluid damper 10 is designed as a linearly moving hydraulic damper. The fluid reservoir may also be designed in alternative configurations, in particular the fluid reservoir may also be acted upon by pressure so that the hydraulic fluid is pressed into the reservoir or pressed out of this counter to a pressure which may also be variable. Instead of a configuration of the fluid damper 10 as a linear piston damper, this may also be designed as rotary hydraulics in which a pivoting piston moves pivotally to and fro. The displacement chambers formed on both sides of the piston then form the respective fluid reservoir for the hydraulic fluid flowing through the housing.

Figure 9A:
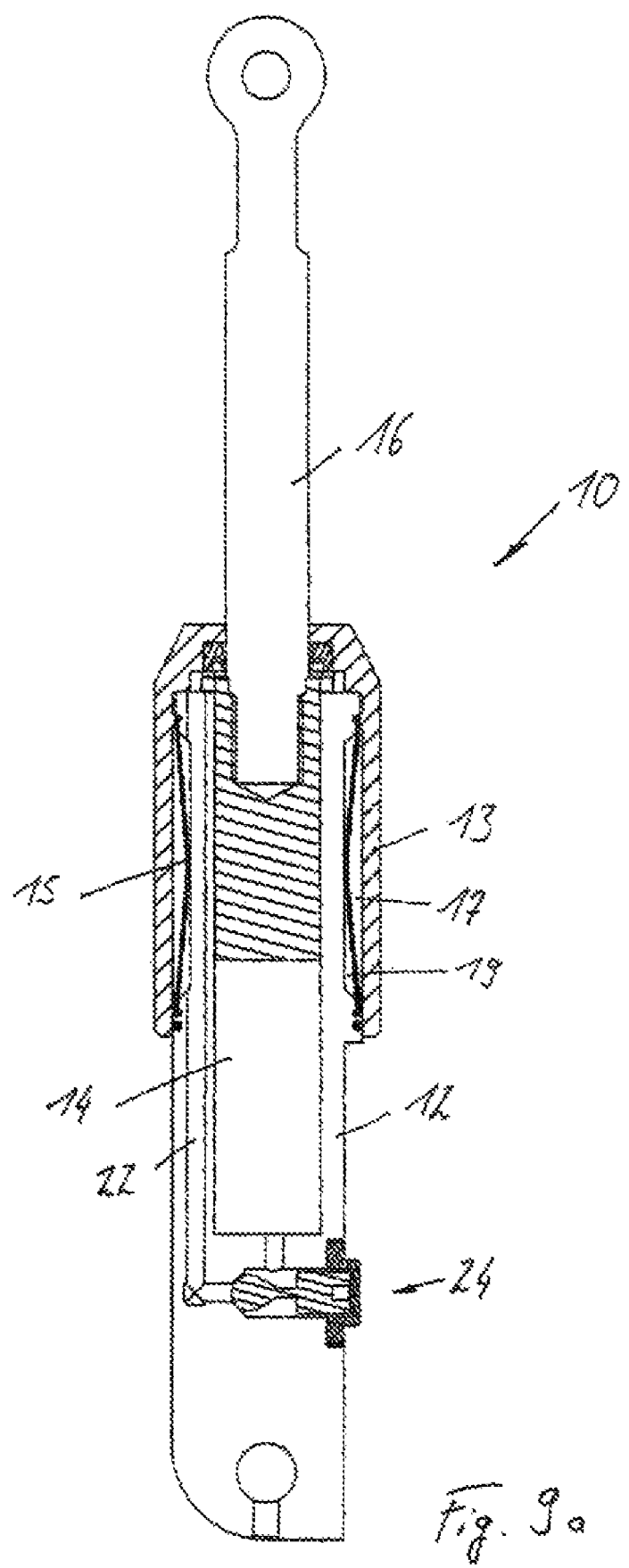
FIGS. 9a, 9b show a further variant of the fluid damper in various positions.
Figure 9B:
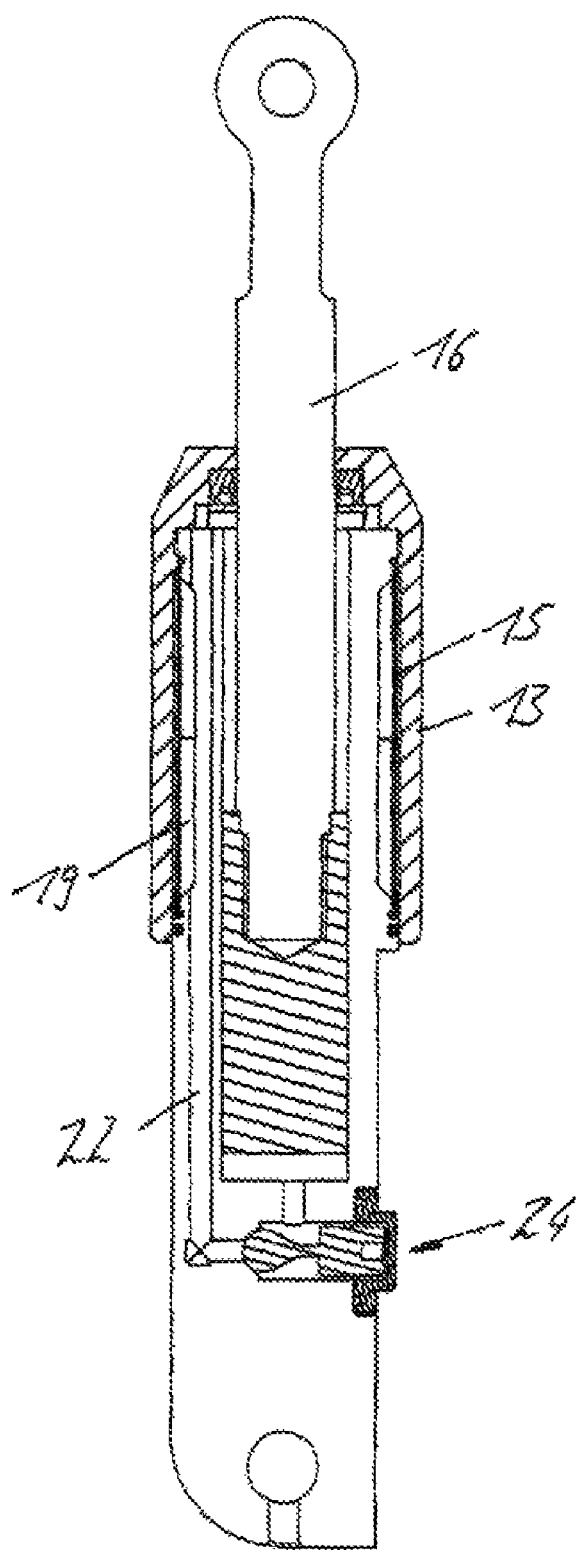

A variant of the fluid damper 10 is illustrated in FIGS. 9a and 9b. FIG. 9a shows the fluid damper 10 in the extended position, and FIG. 9b shows it in the retracted position. Instead of an elastic concertina 18, such as is formed in the exemplary embodiments according to FIGS. 1, 5, 6 and 8, the hydraulic damper according to FIGS. 9a and 9b has a dimensionally stable protective cap 13 which is arranged at the piston-side end of the housing 12. Instead of the concertina 18, a diaphragm 15 is provided, which is designed elastically and can be displaced within the cap 13 in the direction of the housing 12. The diaphragm 15 surrounds an annular gap 19 sealingly, so that a fluid reservoir 19 is formed between the diaphragm 15 and the housing 12. FIG. 9a illustrates the piston 16 in the extended position, so that the hydraulic fluid is collected in the displacement chamber 14. The fluid reservoir 19 assumes a minimum size, this being achieved in that the diaphragm 15 is displaced in the direction of the housing 12. This gives rise, on that side of the diaphragm 15 which faces the cap 13, to a compensating volume 17 which can be filled with air through holes or pressure compensation orifices, not illustrated, in the cap 13. When the piston is retracted, as illustrated in FIG. 9b, a larger volume is required within the fluid reservoir 19, so that the diaphragm 15 is pressed outward in the direction of the cap 13. The air present in the compensating volume 17 is pressed out of the cap 13, with the result that the volume of the fluid reservoir 19 can be increased. In the exemplary embodiment illustrated, the fluid reservoir 19 is connected to the hydraulic fluid circuit via the backflow line 22, but it is also possible, in principle, to provide a corresponding connection via a backflow line 22a provided with a valve 25.

In addition to a one-sidedly acting piston 16, as is shown in the exemplary embodiments illustrated, it is likewise possible to provide a double-sidedly acting piston 16 and to use it in a hydraulic damper 10. The cap 13 serves particularly for ensuring a mechanical protection of the diaphragm 15 which assumes the function of the concertina 18.

Figure 10A:
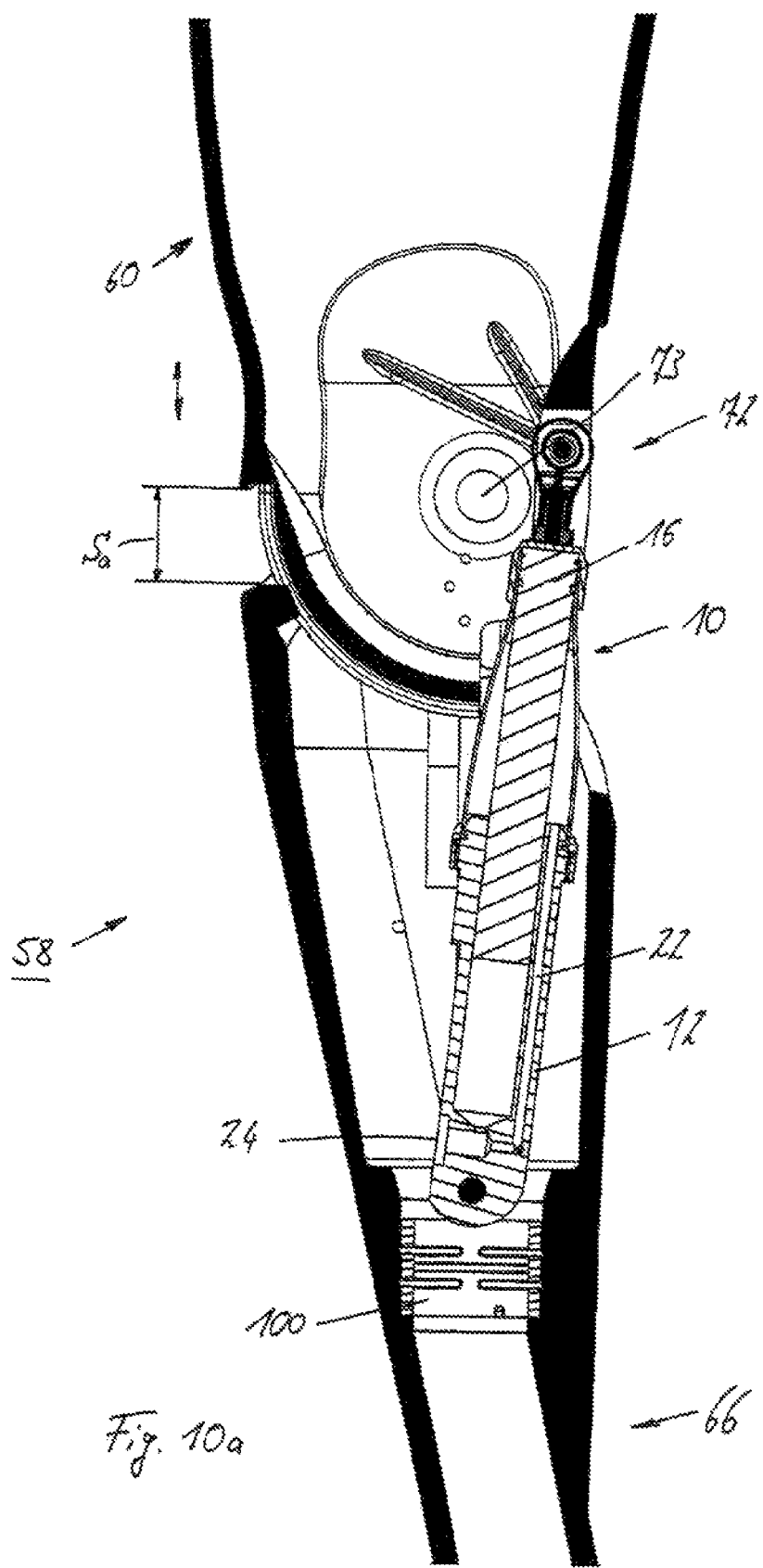
FIGS. 10a, 10b show a leg prosthesis in the non-loaded and the loaded state.
Figure 10B:
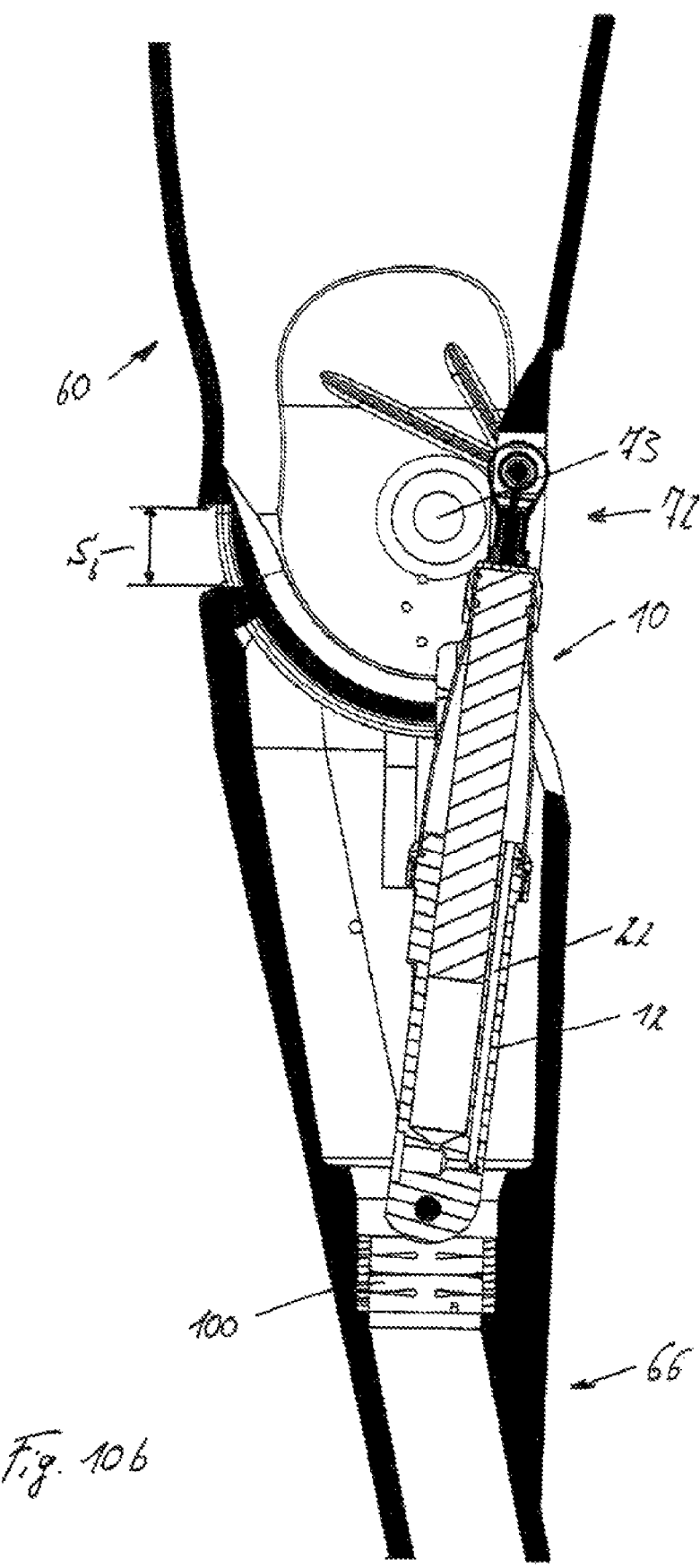

Various load states of a leg prosthesis are illustrated in FIGS. 10a and 10b. FIG. 10a shows a leg prosthesis 58 in a non-loaded state. A thigh part 60 with a knee joint 72 and with a fluid damper 10 mounted thereon is resiliently mounted, via a spring element arranged at the distal end, so as to be displaceable with respect to the lower leg 66. Between the thigh shank 60 and the lower leg shank 66, a gap S is provided, which has the maximum extent $S_a$ in FIG. 10a. If, then, an axial force is exerted on the lower leg 66, the spring element 100 is compressed, as illustrated in FIG. 10b. In the exemplary embodiment illustrated, the spring element 100 is designed as a cylindrical spring element which is compressed to the maximum extent to its block length in FIG. 10b. The gap S is then minimal and is identified in FIG. 10b by reference symbol $S_b$. The difference between $S_a$ and $S_b$ is the displacement travel which corresponds essentially to the spring excursion of the spring 100 or the spring element 100. Owing to the compression of the spring element 100, there follows between the fluid damper 10 and the lower leg 66 a relative movement which may be utilized either for generating a sensor signal for switching a valve or for a direct mechanical switching of the valve. Moreover, the spring 100 causes a slight damping of the tread, while the prosthesis wearer has no feeling of uncertainty on account of a relatively short spring excursion. In the event of axial load, that is to say when the patient is treading or standing, switching is caused such that an increased hydraulic resistance is set in the fluid damper 10 so as to give a patient the highest possible feeling of safety, without a complicated mechanical unlocking of the knee joint having to be carried out in the relieved state, for example during sitting. In the relieved state according to FIG. 10a, a pivoting about the pivot axis 73 of the knee joint 72 can take place, and, in the loaded state according to FIG. 10b, the resistance is increased substantially, ideally locked hydraulically, so that no bending is possible without the destruction of mechanical components.

The selected arrangement of the spring element 100 is in this case very low within the lower leg 66, in order to place the force introduction points as far apart as possible so as to reduce the loads on the mechanical components. The switching of the fluid damper 10 takes place independently of the orientation of the force applied to the lower leg 66, and, after a threshold value of an axial force fraction has been overshot, switching is triggered either via a sensor or via a mechanical device, such as a solenoid valve 24, 25.

If, for example, a fluid damper 10 according to FIGS. 8a and 8b is installed in the leg prosthesis 58, in which the valve 25 is designed as a solenoid valve, direct switching can take place by means of a displacement of a switching magnet with respect to the solenoid valve 25. The solenoid valve 25 is in this case prestressed in the direction of a closing position, so that, after the lapse of a counterforce by the switching magnet, the solenoid valve 25 closes automatically. If, therefore, a switching magnet is arranged in the lower leg 66 and a compression of the spring element 100 is brought about, the housing 12 of the fluid damper 10 is displaced in relation to the lower leg 66 and consequently the solenoid valve 25 is displaced in relation to the switching magnet. If the lower leg 66 is sufficiently loaded, the switching magnet is moved away from the solenoid valve 25 to an extent such that the switching force does not overshoot the prestress, so that the solenoid valve 25 closes. If the lower leg 66 is relieved, the housing 12 moves into the initial position according to FIG. 10 due to the return force of the spring 100 and the solenoid valve 25 is opened. The damping is thereby reduced, because the hydraulic fluid 20 can flow, virtually unimpeded, out of the displacement chamber 14 into the fluid reservoir in the concertina 18. In the exemplary embodiment according to FIGS. 10a and 10b, the fluid damper 10 has a concertina, but alternatively to this a fluid damper according to FIGS. 9a and 9b may also be used, with a cap 13 as mechanical protection either of the concertina 18 or of the diaphragm 15. Basically, however, the fluid damper 10 according to FIGS. 1a and 1b is also possible and provided, and a fluid damper according to FIGS. 1a and 1b may likewise be provided with a protective cap 13 against damage to the concertina 18. Alternatively to a solenoid valve, the actuation of a valve may also take place by means of a buckling spring, a slotted guide or a lever mechanism.

Alternatively to the illustrated embodiment of the spring element, other telescopic devices and spring elements may be provided, which allow a relative displacement of the thigh 60 or thigh shank 60 and of the lower leg 66 with respect to one another. In the exemplary embodiment according to FIGS. 10a and 10b, the knee joint 72, together with the fluid damper 10 and with a strut, not illustrated in any more detail, is designed as a kind of frame and is mounted on the thigh or thigh shank 60, so that these components can be displaced together in relation to the lower leg 66. The arrangement of the spring element 100 in the lower leg 66 is not mandatory, and basically another relative displacement between the lower leg 66 and damper 10 may also be implemented.

Figure 11:
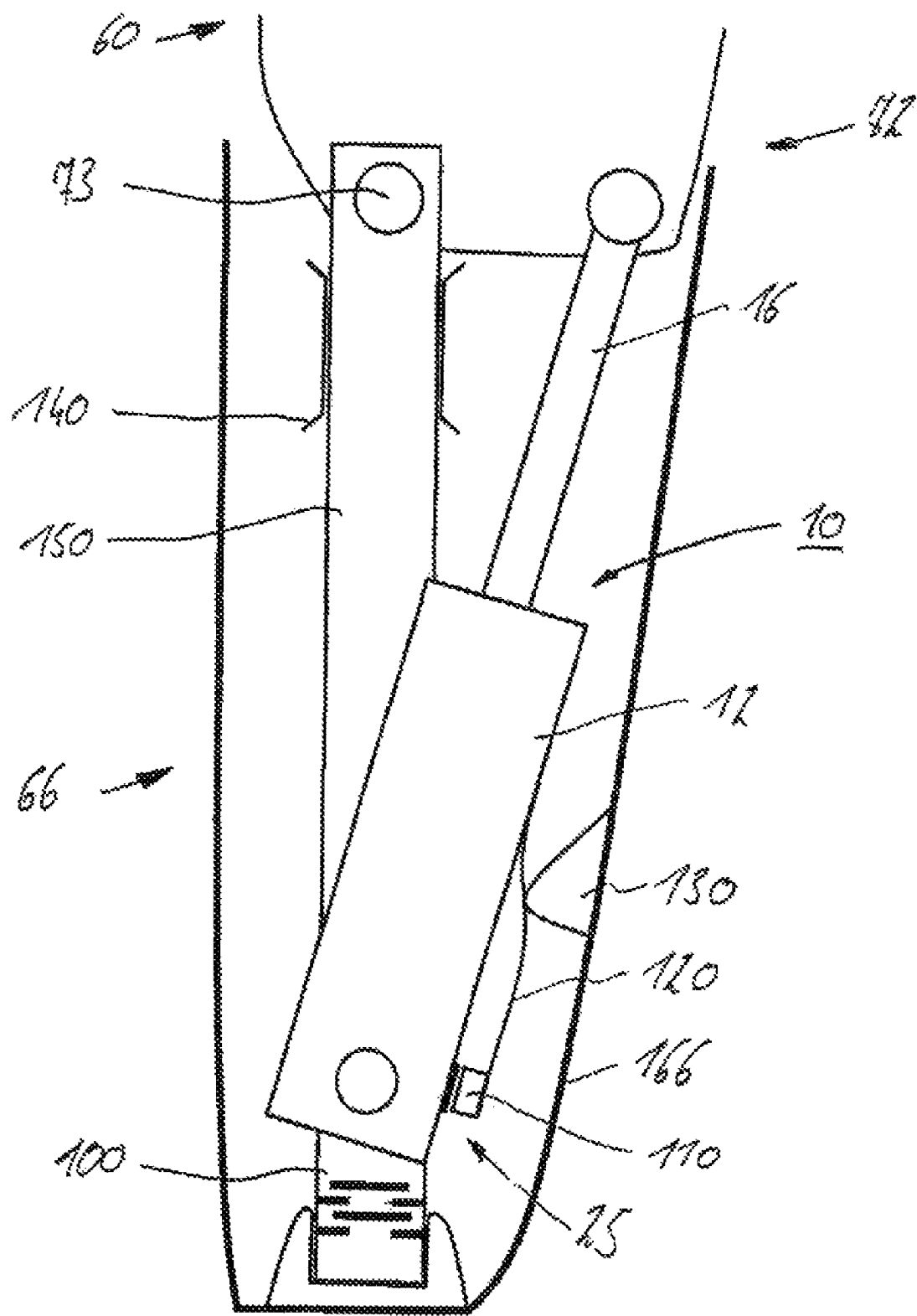
FIG. 11 shows a variant of the leg prosthesis with angle-dependent hydraulic switching.

FIG. 11 illustrates diagrammatically a variant of the invention. A thigh shank 60 is connected to a lower leg 66 pivotably via the axis of rotation 73 of the knee joint 72. The lower leg 66 has a housing 166, within which the hydraulic damper 10 and a bar 150 are mounted. The bar 150 carries the axis of rotation 73 at its proximal end and the spring element 100 at its distal end. The distal end of the housing 12 is likewise mounted on this bar 150. The proximal end of the piston 16 is arranged on the thigh shank 60 or thigh 60. Within the housing 166 is arranged a cam 130 which projects in the direction of the damper housing 12. A switching magnet 110 is mounted resiliently on the housing 12 via a spring tongue 120. The switching magnet 110 lies opposite the solenoid valve 25.

An axial guide 140 for the bar 150 is likewise provided within the housing 166 and ensures that the bar 150 moves only axially, so that a lateral displacement of the bar 150 and consequently of the knee joint 120 and thigh 60 or thigh shank 60 in relation to the lower leg 66 is avoided. When an axial force which has a sufficiently high component in the direction of the axis of rotation 73 is exerted on the lower leg 66, the spring element 100 is compressed, so that the spring tab 120 is displaced in relation to the cam 130. On account of the curved form of the spring tab 120, the pressure decreases in the event of an increasing axial displacement in the distal direction, so that the switching magnet 110 is moved increasingly away from the solenoid valve 25 as a result of the return force of the spring tab 120. As soon as the switching magnet 110 has been moved sufficiently far from the solenoid valve 25, the solenoid valve 25 closes instantaneously and increases the damping abruptly. The same mechanism may also be employed for the angle-dependent control of the damper force. If the thigh 60 or thigh shank 60 is pivoted about the pivot axis 73, the bearing point of the piston 16 on the thigh shank 60 executes a circular movement which, in addition to a vertical component, also has a horizontal component. Via the horizontal displacement of the piston 16 and, along with this, of the housing 12, the switching cam 130 is moved away from the spring tab 120, so that, with an increasing pivot angle φ of the thigh 60 in relation to the lower leg 66, the solenoid valve 25 is activated in that the switching magnet 110 is displaced away from the housing 12. The embodiment illustrated has the advantage that, in the event of a failure of the control, for example if the spring tongue 120 breaks or an unwanted axial displacement occurs, the damping is increased instantaneously so that the knee joint 72 is kept stable. This is extremely important for geriatric patients so that they feel safe.

In addition to a magnetic activation of the valve 25, other mechanical couplings may also take place, for example via cam disks, slotted guides or lever devices, which close the valve in the event of a sufficient displacement in the axial direction or sufficient bending.

The spring element 100 is designed as a spring block which, in addition to making available a displacement travel between the thigh shank 60 and the lower leg shank 66, also serves for absorbing transverse forces and for avoiding possible play within the joint 72 or the prosthesis 58. The block spring 100 can absorb transverse forces and provides a certain tread damping, while at the same time a stop and limit the axial displacement travel that can be set via the spring 100.

The use of a fluid damper in a geriatric knee joint has hitherto been considered too complicated, but it has become apparent that fluid dampers are highly suitable, since they have no "stick/slip" effect which occurs in other mechanical interlocks or braking devices. In addition to the illustrated mechanical switching of the valve 25, electronic detection of a displacement or axial force and a corresponding actuation of the valve via an actuator are likewise possible. The angle-dependent control applies a relatively high resistance to the joint 70 from a relatively small bending angle, in order to provide high damping and standing phase safety at a relatively early stage. The switching threshold at which the valve 25 closes and provides increased resistance can be set and preferably lies between a 20° and 50° bending angle. Within this angular range of 20° to 50°, there is a switch from a relatively low resistance within the fluid damper to a high resistance.

LIST OF REFERENCE SYMBOLS

10 Fluid damper
12 Cylinder housing
13 Cap
14 Displacement chamber
15 Diaphragm
16 Piston
17 Free space
18 Concertina
19 Fluid reservoir
20 Hydraulic fluid
22 Backflow line
22a Backflow line
24 Valve
25 Valve
26 Annular gap
28 Annular-gap fluid path
28a Fluid path backflow
29 Seal
30 Backflow-line fluid path
32 Valve seat
34 Valve ball
36 Helical spring
38 Backflow path
40 End
42 End face
44 Pin
46 Actuator diaphragm
48 Actuator basic body
50 Bypass line
52 Bypass valve
54 Bypass-line fluid path
56 Electromagnet
58 Leg prosthesis
60 Thigh
62 Proximal thigh end
64 Distal thigh end
66 Lower leg
68 Proximal lower leg end
70 Distal lower leg end
72 Knee joint
73 Axis of rotation
74 Front foot
76 Back foot
78 Front-foot force sensor
80 Back-foot force sensor
82 Electric control
84 Leg-axis force sensor
86 Sleeve
88 Measuring piston
90 Filling material
92a,b Measuring elements
94 Elastic element
96a,b Webs
100 Spring element
110 Magnet
120 Spring
130 Cam
140 Guide
150 Bar
166 Housing
T Push-in depth
$F_E$ Push-in force
$F_A$ Pull-out force
$F_B$ Leg-axis force
$F_V$ Front-foot force
$F_F$ Heel force
E Penetration portion
A Free portion
L Longitudinal angle
φ Pivot angle
S Displacement travel

The invention claimed is:
1. An orthopaedic having an orthopaedic fluid damper comprising:
(a) a displacement chamber formed in a housing,
(b) a piston mounted in the displacement chamber,
(c) a fluid reservoir for a fluid,

(d) a backflow line which connects the displacement chamber to the fluid reservoir, (e) a valve which can assume an opening position and a closing position, in which the valve is operative to at least partially close the backflow line, (f) a joint which has a first limb and a second limb, the first limb being connected to the piston, (g) a bar attached at a proximal end to the first limb of the joint at a point of axial rotation and resiliently attached at a distal end to the second limb so as to allow only axial movement of the second limb with respect to the bar, the housing being connected to the distal end of the bar, and (h) a force sensing device for detecting a joint force ($F_B$) acting on the joint, which is designed in order to bring the valve into the closing position when the joint force ($F_B$) overshoots a preset threshold value.

2. The orthopaedic aid as claimed in claim 1, wherein the orthopaedic aid is a leg prosthesis with a knee joint, and the force sensing device for detecting the joint force acting on the knee joint is a leg-axis force sensor for detecting a leg-axis force acting in the axial direction (L) of the leg prosthesis.

3. The orthopaedic aid as claimed in claim 2, further comprising an electric control which is connected electrically to the leg-axis force sensor and is designed for the electrical activation of the valve.

4. The orthopaedic aid as claimed in claim 1, wherein the force sensing device for detecting the joint force is set up mechanically and, when loaded, displaces the valve into the closing position.

5. The orthopaedic aid as claimed in claim 4, wherein the force sensing device for detecting the joint force is designed as a buckling spring, spring, cam guide or slotted guide or as a lever system.

6. The orthopaedic aid as claimed in claim 4, the force sensing device is coupled to a solenoid valve.

7. The orthopaedic aid as claimed in claim 4, wherein the force sensing device is designed such that displacement dependent on a pivot angle ϕ of the limbs with respect to one another causes actuation of a switching element in relation to the valve.

8. The orthopaedic aid as claimed in claim 1, wherein the two limbs are mounted one on the other so as to be axially displaceable to a limited extent in relation to one another.

9. The orthopaedic aid as claimed in claim 1, wherein the resilient attachment of the bar and the second limb is a spring acting in the axial direction and the spring acts counter to an axial displacement of the first and second limbs toward one another.

10. The orthopaedic aid as claimed in claim 1, wherein the damper and the first limb of the joint are mounted together on the bar so as to be displaceable in relation to the second limb.

11. The orthopaedic aid as claimed in claim 10, wherein the resilient attachment of the bar and the second limb is a spring arranged between the bar and the second limb and acts counter to a displacement of the second limb towards the bar.

12. The orthopaedic aid as claimed in claim 10, wherein the damper and the first limb of the joint are mounted together on the bar which is shiftable, in relation to the second limb.

13. The orthopaedic aid as claimed in claim 1, wherein the hydraulic damper is designed as a cylinder.

14. The orthopaedic aid as claimed in claim 1, wherein the orthopaedic aid is a prosthesis or orthesis.

15. A method for controlling an orthopaedic aid as claimed in claim 1, with the steps:
(a) detection of the joint force ($F_B$) acting on the joint, and
(b) activation of the valve such that it at least partially closes the backflow line.

16. The method as claimed in claim 15, wherein the joint is a knee joint, and the detected joint force is a leg-axis force ($F_B$) which acts in the axial direction (L) of the leg prosthesis.

17. The method as claimed in claim 16, wherein the valve is activated such that it at least partially closes the backflow line when the leg-axis force ($F_B$) overshoots a preset closing threshold value.

18. The method as claimed in claim 15, wherein the valve is activated such that it enables the backflow line when the leg-axis force ($F_B$) undershoots a preset enabling threshold value.

19. The method as claimed in claim 15, wherein the valve is switched independently of a position of the limbs.

20. The method as claimed in claim 15, wherein the valve is switched as a function of an angle ϕ of the limbs.

21. The method as claimed in claim 15, wherein the valve is switched mechanically such that a relative movement of the limbs in relation to one another is transmitted to the valve.

\* \* \* \* \*